United States Patent
Olivier-Bourbigou et al.

(10) Patent No.: US 7,781,621 B2
(45) Date of Patent: Aug. 24, 2010

(54) HYDROFORMYLATION METHOD INVOLVING A COBALT-BASED CATALYST IN A NON-AQUEOUS IONIC LIQUID

(75) Inventors: Helene Olivier-Bourbigou, Saint Genis-Laval (FR); Lucien Saussine, Charly (FR); Lionel Magna, Lyons (FR); David Proriol, Paris (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 12/373,409

(22) PCT Filed: Jun. 22, 2007

(86) PCT No.: PCT/FR2007/001052

§ 371 (c)(1),
(2), (4) Date: Aug. 24, 2009

(87) PCT Pub. No.: WO2008/006951

PCT Pub. Date: Jan. 17, 2008

(65) Prior Publication Data

US 2010/0010270 A1    Jan. 14, 2010

(30) Foreign Application Priority Data

Jul. 13, 2006    (FR) .................................... 06 06497

(51) Int. Cl.
   *C07C 45/50*    (2006.01)
(52) U.S. Cl. ....................................... 568/454; 568/455
(58) Field of Classification Search .................. 568/451, 568/454

See application file for complete search history.

(56) References Cited

U.S. PATENT DOCUMENTS

| 5,874,638 | A  | * | 2/1999  | Chauvin et al. ............. 568/454 |
| 6,469,216 | B2 | * | 10/2002 | Hillebrand et al. .......... 568/454 |
| 6,617,474 | B2 | * | 9/2003  | Favre et al. ................. 568/451 |
| 7,060,860 | B2 | * | 6/2006  | Magna et al. ............... 568/454 |
| 7,223,374 | B2 | * | 5/2007  | Magna et al. ............... 422/224 |
| 2001/0039363 | A1 | | 11/2001 | Hillebrand et al. |
| 2003/0225303 | A1 | | 12/2003 | Magna et al. |

FOREIGN PATENT DOCUMENTS

| EP | 1106595 A1 | 6/2001 |
| FR | 2838431 A1 | 10/2003 |

* cited by examiner

*Primary Examiner*—Sikarl A Witherspoon
(74) *Attorney, Agent, or Firm*—Millen, White, Zelano & Branigan, P.C.

(57) ABSTRACT

In a method for hydroformylating olefinically unsaturated compounds by means of a cobalt-based catalyst, used in a non-aqueous ionic liquid, liquid at a temperature below 100° C. and comprising at least one cation $Q^+$ and at least one anion $A^-$, said method comprising at least a stage of reaction under pressure and at least a stage of separation of the phases by decantation, recycling of the catalyst is improved:
   through the use of a ligand selected from among the Lewis bases, more particularly pyridine derivatives,
   and simultaneously through the addition of this ligand in a post-reaction stage.

Figure 1:
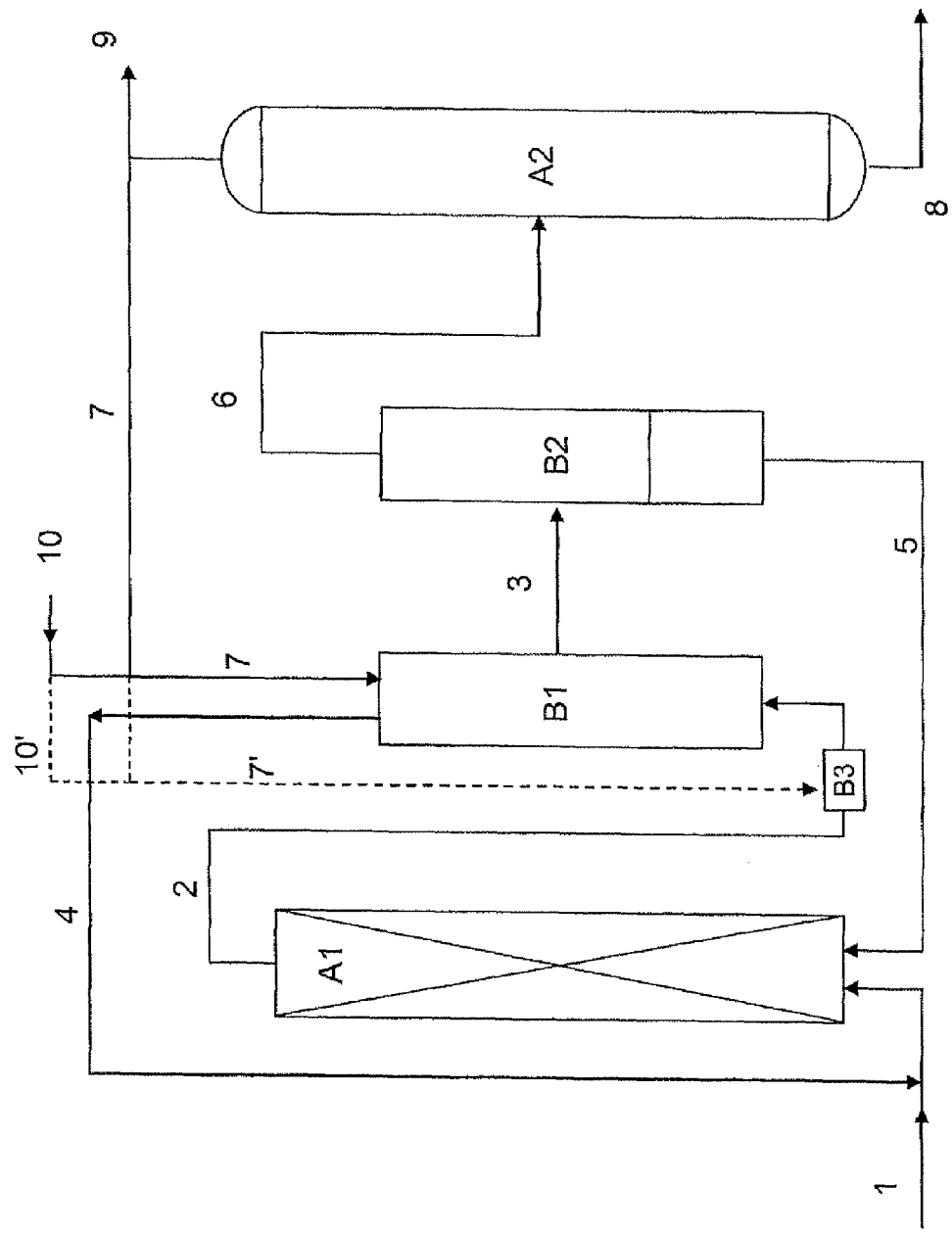

At the end of this process, the organic phase containing the reaction products can be recovered and the ionic liquid phase containing the catalyst can be recycled to the hydroformylation reactor.

38 Claims, 2 Drawing Sheets

HYDROFORMYLATION METHOD INVOLVING A COBALT-BASED CATALYST IN A NON-AQUEOUS IONIC LIQUID

FIELD OF THE INVENTION

The present invention relates to a method for hydroformylating olefinically unsaturated compounds by means of a cobalt-based catalyst used in a non-aqueous ionic liquid, comprising at least one cation $Q^+$ and at least one anion $A^-$, with improved catalyst recycling.

Hydroformylation of olefinic compounds is a reaction of high industrial importance and most methods involve homogeneous catalysts dissolved in an organic phase consisting of the reactants, the products and possibly of excess ligand, so that one has difficulty in separating and recovering the catalyst, in particular when it is used in relatively large amounts, as it is the case with methods using a cobalt-based catalyst.

BACKGROUND OF THE INVENTION

One solution for solving this problem was mentioned by Bartik et al.: Organometallics (1993) 12 164-170, J. Organometal. Chem. (1994) 480 15-21, and by Beller et al.: J. Molecular Catal. A: Chemical (1999) 143 31-39. It consists in carrying out hydroformylation in the presence of an aqueous solution containing a cobalt complex made hydrosoluble by the presence of a phosphine-sulfonate ligand, such as the sodium salt of trisulfonated triphenylphosphine or of a trisulfonated tris-(alkylphenyl)-phosphine. The organic phase containing the aldehydes is thus readily separated from the aqueous phase containing the catalyst.

Despite the significance of these various systems, the low capacity of water to dissolve some organic substrates such as long-chain olefins is a major limitation for these methods. Hydroformylation of this type of feeds very often leads to low reaction rates, making any industrial application unthinkable. Furthermore, water is a very coordinating protic solvent that can be reactive to catalysts. Although it is of great interest, the use of water as the reaction solvent cannot be generalized to all catalyst and substrate types.

It is described in U.S. Pat. No. 5,874,638 filed by the applicant that some limitations linked with the use of water as the reaction solvent (in particular the solubility of long olefins) can be overcome by dissolving some catalytic compounds of transition metals from groups 8, 9 and 10, known for catalyzing hydroformylation, in non-aqueous ionic liquids consisting of organic-inorganic salts liquid at ambient temperature.

However, when the catalyst comprises a cobalt salt or complex, it is very difficult to prevent at least partial formation of dicobalt octacarbonyl and/or cobalt tetracarbonyl hydride under the conditions of the hydroformylation reaction. These two compounds being soluble in the organic reaction phase consisting of at least the olefinic reactant and the aldehydes produced, cobalt recycling by means of the non-aqueous ionic liquid phase is only partial, which leads to catalyst losses.

Besides, it has been shown in U.S. Pat. No. 6,617,474 filed by the applicant that it is possible to increase the reaction rates by carrying out the reaction in an ionic liquid that is partly or entirely miscible with the reaction products, while keeping the advantage of the separation and re-use of the ionic liquid containing the catalyst and improving the recovery of the reaction products, by injecting after the reaction section an organic solvent, weakly or non-miscible with the ionic liquid, which can advantageously be the olefinically unsaturated compound to be hydroformylated and which improves demixing of the reaction effluent products.

In this context, it has been found and described in patent application US-A-2003/0,225,303 filed by the applicant that, in the hydroformylation reaction catalyzed by cobalt complexes used in a non-aqueous ionic liquid, recycling the metal in the ionic liquid is greatly improved by the use of a ligand selected from among the Lewis bases and simultaneously by means of an intermediate depressurization stage between the reaction stage under pressure and the stage of phase separation by decantation. At the end of this depressurization stage, the organic phase is separated in the decantation stage and the non-aqueous ionic liquid phase containing the catalyst can be re-used.

It has now been found that it is possible to greatly improve the reaction rate, on the one hand, and the retention and recycle of the cobalt-based catalyst in the ionic liquid phase, on the other hand, by addition of the ligand in a post-reaction stage. The present invention thus provides a new implementation of the system, notably intended to combine a high reaction rate and improved catalyst retention and recycle.

DETAILED DESCRIPTION

The method of hydroformylation in the liquid phase of olefinically unsaturated compounds according to the invention can thus be defined in that it comprises:

a reaction stage carried out in the presence of at least one non-aqueous ionic liquid comprising at least one salt of general formula $Q^+A^-$, wherein $Q^+$ represents a cation and $A^-$ represents an anion, and of a catalyst comprising at least one cobalt complex with at least one ligand L selected from among the Lewis bases, a depressurization stage, a decantation stage, and a recycling stage, said method being characterized in that the addition of ligand L, possibly in admixture with an organic solvent, is carried out in a post-reaction stage, and in that the molar ratio of ligand L to cobalt compound (L/Co) in this post-reaction stage is above 2:1 and preferably below 100:1.

The unsaturated olefinic compounds likely to be hydroformylated are selected from among mono-olefins, diolefins and particularly conjugate diolefins, the olefinic compounds comprising one or more heteroatoms, notably unsaturated, such as the ketone function or carboxylic acid.

Non limitative examples thereof are the hydroformylation of pentenes to hexanal and methylpentanal, of hexenes to isoheptanals, of iso-octenes to isononanals, of isodecenes to iso-undecanals, of olefinic $C_{11}$ to $C_{16}$ cuts to $C_{12}$ to $C_{17}$ aldehydes. These olefinic compounds can be used pure or diluted by saturated or unsaturated hydrocarbons. They can notably come from olefin conversion processes such as dimerization and oligomerization of olefins (in particular C2-C5 olefins), and from any other process leading to the production of an olefin mixture. Non limitative examples of potential feeds to be hydroformylated according to the method of the invention are olefins resulting from Dimersol®, Difasol®, Octol® or SHOP® processes.

This process can be used for feeds to be hydroformylated consisting of predominantly internal mono-olefins, i.e. for mixtures of mono-olefins containing at most 30% terminal mono-olefins Octene mixtures having the composition as follows can be mentioned in particular:

linear octenes (2 to 10% by weight),
methylheptenes (50 to 70% by weight),
dimethylhexenes (25 to 35% by weight),
other mono-olefins (1 to 3% by weight)
wherein less than 10% are terminal mono-olefins.

In order to improve separation of the reaction products and of the ionic liquid, it is possible to use an organic solvent as a complement to the reaction mixture described above. This solvent addition is preferably performed in a post-reaction stage. This organic solvent is more particularly selected from among the aliphatic hydrocarbons, cyclic or acyclic, saturated or unsaturated, and the aromatic or substituted aromatic hydrocarbons. Among the latter, the organic solvent can preferably be selected from among the n-paraffins and iso-paraffins and the cyclic aliphatic hydrocarbons. More preferably, the organic solvent can consist of the olefinically unsaturated compound(s) to be converted. It can be used to add the ligand.

The catalyst precursor cobalt compounds are selected from among the cobalt salts, such as acetylacetonates, alcoholates, carboxylates and in particular formiate or acetate, and the carbonyl complexes, such as dicobaltoctacarbonyl, cobalt tetracarbonyl hydride and carbonyl clusters. Selection of the catalyst precursor compound is not critical.

The Lewis basic ligand is selected from among the oxygen-containing ligands, the sulfur-containing ligands, the nitrogen-containing ligands and the phosphorus-containing ligands, substituted or not by ionic functional groups. The ionic functional groups are selected from among the sulfonates, carboxylates, phosphates, ammoniums, phosphoniums and imidazoliums.

The oxygen-containing ligands are more particularly selected from among the alcohols, phenols, ethers, ketones and acetals. Non limitative examples thereof are methanol, ethanol, phenol, diethylether, dibutylether, diphenylether, tetrahydrofurane, dioxane-1,4, dioxolane-1,3, glyme, diglyme, acetone, methyethylketone, acetophenone, methylal, dimethoxy-2,2 propane and di(ethyl-2hexyloxy)-2,2 propane.

The sulfur-containing ligands are more particularly selected from among the thiols, thiophenols, thioethers and disulfides. Non limitative examples thereof are methanethiol, ethanethiol, thiophenol, diethylsulfide, dimethyldisulfide and tetrahydrothiophene.

The nitrogen-containing ligands are more particularly selected from among the mono-amines, di-, tri- and poly-amines, imines, di-imines, pyridines, bipyridines, imidazoles, pyrroles and pyrazoles. Preferentially, the pyridine type ligand is selected from among the non-substituted pyridines and the pyridines substituted in position 2, 3, 4 or 5 by alkyl, aryl, aralkyl, alcoxy, aryloxy, hydroxy, halogenide, carboxyalkyl groups. Non limitative examples thereof are methylamine, trimethylamine, triethylamine, ethylenediamine, diethylenetriamine, diazabicyclo-octane, N,N'-dimethyl-ethane-1,2-diimine, N,N'-di-t-butyl-ethane-1,2-diimine, N,N'-di-t-butyl-butane-2,3-diimine, N,N'-diphenyl-ethane-1,2-diimine, N,N'-bis-(dimethyl-2,6-phenyl)-ethane-1,2-diimine, N,N'-bis-(diisopropyl-2,6-phenyl)-ethane-1,2-diimine, N,N'-diphenyl-butane-2,3-diimine, N,N'-bis-(dimethyl-2,6-phenyl)-butane-2,3-diimine, N,N'-bis-(diisopropyl-2,6(phenyl)-butane-2,3-diimine, pyridine, 2-picoline, 4-picoline, t-butyl-2-pyridine, t-butyl-4-pyridine, butyl-3-pyridine, phenyl-2-pyridine, phenyl-3-pyridine, phenyl-4-pyridine, benzyl-2-pyridine, benzyl-4-pyridine, methoxy-2-pyridine, methoxy-3-pyridine, methoxy-4-pyridine, di(t-butyl)-2,6-pyridine, 2,2'-bipyridine, 4,4'-bipyridine, di(phenyl)-2,6-pyridine, (phenyl-3-propyl)-4-pyridine, imidazole, N-methylimidazole, N-butylimidazole, pyrrole, N-methylpyrrole and dimethyl-2,5-pyrrole.

The phosphorus-containing ligands are more particularly selected from among the phosphines, polyphosphines and phosphine oxides, phosphites. Non limitative examples thereof are tributylphosphine, trisopropylphosphine, tricyclohexylphosphine, triphenylphosphine, tris(o-tolyl)phosphine, bis(diphenyl-phosphino)ethane, trioctyl-phosphine oxide, triphenylphosphine oxide and triphenylphosphite.

The preferred ligands are more particularly selected from among the pyridine derivatives. Non limitative examples thereof are pyridine, 2-methylpyridine, 3-methylpyridine, 4-methylpyridine, 2-methoxypyridine, 3-methoxypyridine, 4-methoxy-pyridine, 2-fluoropyridine, 3-fluoropyridine, 3-trifluoromethylpyridine, 2-phenyl-pyridine, 3-phenylpyridine, 2-benzylpyridine, 3,5-dimethylpyridine, 2,6-diterbutyl-pyridine and 2,6-diphenylpyridine, quinoline and 1,10-phenanthroline.

The catalytic composition is obtained by mixing, in any way, ionic liquid with the cobalt compound and the ligand. The transition metal compound and/or the ligand can also be first dissolved in an organic solvent.

The complex that forms from the cobalt precursor and the ligand can be prepared prior to the reaction by mixing the cobalt precursor with the ligand in a suitable solvent, an organic solvent for example, or in the non-aqueous ionic liquid that will be used thereafter in the catalytic reaction. The complex can also be prepared in situ by mixing the cobalt precursor and the ligand directly in the hydroformylation reactor.

The concentration of the cobalt complex in the non-aqueous ionic liquid is not critical. It advantageously ranges between 0.1 mmole (in cobalt atoms) per liter and 10 moles per liter of ionic liquid, preferably between 10 mmoles and 5 moles per liter, and more preferably between 50 mmoles and 1 mole per liter.

The ratio of the partial pressures of hydrogen to carbon monoxide used in the reaction medium for hydroformylation can be 10:1 to 1:10, preferably 1:1, but any other ratio can be used in the implementation of the method.

The temperature at which hydroformylation is carried out will range between 30° C. and 250° C. It is advantageously below 200° C. and it preferably ranges between 50° C. and 180° C. The pressure can range between 1 MPa and 30 MPa, preferably between 2 MPa and 20 MPa.

The catalytic reaction of hydroformylation of the unsaturated compounds can be carried out with one or more reaction stages. In a continuous embodiment, the effluent from the reactor under pressure is transferred to a zone where it is depressurized to a pressure below 1 MPa, preferably to the atmospheric pressure, at a temperature at most equal to 150° C. and preferably below 60° C. Contact between the two liquid phases can be maintained in this stage by mechanical stirring or by any other suitable means. The contact time in the depressurization zone and the pressure and temperature conditions must be suitably selected to best provide transfer of the catalyst to the non-aqueous ionic liquid phase.

At the depressurization zone outlet, the organic phase containing the reaction products is separated, advantageously by simple decantation of the non-aqueous ionic liquid phase containing almost all of the catalyst. This ionic liquid phase that contains the catalyst is at least partly sent back to the reactor, and the other part can be treated by distillation so as to suitably separate the various components of the system.

In the non-aqueous ionic liquid of formula $Q^+A^-$ used in the method according to the invention, $Q^+$ represents a cation preferably selected from among the quaternary sulfonium, quaternary guanidinium, quaternary ammonium and quaternary phosphonium, and A⁻ represents an anion preferably selected from among the following anions: halogenides, nitrate, sulfate, alkylsulfates, phosphate, alkylphosphates, acetate, halogeno-acetates, tetrafluoroborate, tetrachloroborate, hexafluorophosphate, trifluoro-tris-(pentafluoroethyl)phosphate, hexafluoroantimonate, fluorosulfonate, alkylsulfonates (methylsulfonate for example), perfluoroalkylsulfonates (trifluoromethylsulfonate for example), bis(perfluoroalkylsulfonyl)amidides (for example bis trifluoromethylsulfonyl amidide of formula $N(CF_3SO_2)_2^-$), tris-trifluoromethylsulfonyl methylide of formula $C(CF_3SO_2)_3^-$, bis-trifluoromethylsulfonyl methylide of formula $HC(CF_3SO_2)_2^-$, arenesulfonates, possibly substituted by halogen or halogeno-alkyl groups, the tetraphenylborate anion and the tetraphenylborate anions whose aromatic rings are substituted, tetra(trifluoroacetoxy)borate, bis(oxalato)borate, dicyanamide, tricyanomethylide, as well as the tetrachloro-aluminate anion.

The cations $Q^+$ are preferably selected from among the quaternary sulfonium, quaternary guanidinium, quaternary phosphonium and quaternary ammonium.

In the formulas hereafter, $R^1$, $R^2$, $R^3$, $R^4$, $R^5$ and $R^6$ each represent hydrogen (except for the $NH_4^+$ cation for $NR^1R^2R^3R^4$), preferably a single substituent representing hydrogen, or hydrocarbyl radicals having 1 to 30 carbon atoms, for example alkyl groups, saturated or non-saturated, cycloalkyls or aromatics, aryls or aralkyls, possibly substituted, comprising 1 to 30 carbon atoms.

$R^1$, $R^2$, $R^3$, $R^4$, $R^5$ and $R^6$ can also represent hydrocarbyl radicals carrying one or more functions selected from among the following functions: —CO₂R, —C(O)R, —OR, —C(O)NRR', —C(O)N(R)NR'R", —NRR', —SR, —S(O)R, —S(O)₂R, —SO₃R, —CN, —N(R)P(O)R'R', —PRR', —P(O)RR', —P(OR)(OR'), —P(O)(OR)(OR'), wherein R, R' and R", identical or different, represent each hydrogen or hydrocarbyl radicals having 1 to 30 carbon atoms.

The quaternary sulfonium and quaternary guanidinium cations preferably meet one of the following general formulas:

$SR^1R^2R^{3+}$ and $C(NR^1R^2)(NR^3R^4)(NR^5R^6)^+$ where $R^1$, $R^2$, $R^3$, $R^4$, $R^5$ and $R^6$, identical or different, are defined as above.

The quaternary ammonium and/or phosphonium cations $Q^+$ preferably meet one of the following general formulas: $NR^1R^2R^3R^{4+}$ and $PR^1R^2R^3R^{4+}$, or one of the general formulas: $R^1R^2N=CR^3R^{4+}$ and $R^1R^2P=CR^3R^{4+}$ wherein $R^1$, $R^2$, $R^3$ and $R^4$, identical or different, are defined as above.

The quaternary ammonium and/or phosphonium cations can also be derived from nitrogen-containing and/or phosphorus-containing heterocycles comprising 1, 2 or 3 nitrogen and/or phosphorus atoms, of general formlas:

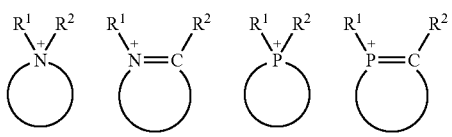

wherein the cycles consist of 4 to 10 atoms, preferably 5 to 6 atoms, and $R^1$ and $R^2$, identical or different, are defined as above.

The quaternary ammonium or phosphonium cation can also meet one of the general formulas as follows:

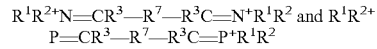

wherein $R^1$, $R^2$ and $R^3$, identical or different, are defined as above, and $R^7$ represents an alkylene or phenylene radical.

Examples of $R^1$, $R^2$ and $R^3$ groups are: the methyl, ethyl, propyl, isopropyl, primary butyl, secondary butyl, tertiary butyl, amyl, phenyl or benzyl radicals; $R^7$ can be a methylene, ethylene, propylene or phenylene group.

Preferably, the quaternary ammonium and/or phosphonium cation $Q^+$ is selected from among: N-butylpyridinium, N-ethylpyridinium, pyridinium, ethyl-3-methyl-1-imidazolium, butyl-3-methyl-1-imidazolium, hexyl-3-methyl-1-imidazolium, butyl-3-dimethyl-1,2-imidazolium, ethyl-3-dimethyl-1,2-imidazolium, N-butylimidazolium, N-ethylimidazolium, the (hydroxy-2-ethyl)-1-methyl-3-imidazolium cation, the (carboxy-2-ethyl)-1-methyl-3-imidazolium cation, diethylpyrazolium, N-butyl-N-methylpyrrolidinium, N-ethyl-N-methylpyrrolidinium, N-butyl-N-methylmorpholinium, trimethylphenylammonium, trimethylpropylammonium, triethylammonium, tetrabutylphosphonium and tributyl-tetradecyl-phosphonium.

Examples of salts that can be used according to the invention are butyl-3-methyl-1-imidazolium bis(trifluoromethylsulfonyl)amidide, ethyl-3-methyl-1-imidazolium bis(trifluoromethylsulfonyl)amidide, triethylammonium bis(trifluoromethyl-sulfonyl)amidide, trimethylpropylammonium bis(trifluoromethylsulfonyl)amidide, butylimidazolium bis(trifluoromethylsulfonyl)amidide, butyl-3-dimethyl-1,2-imidazolium bis(trifluoromethylsulfonyl)amidide, N-butyl-N-methylpyrrolidinium bis(trifluoromethylsulfonyl)amidide, N-ethyl-N-methylpyrrolidinium bis(trifluoro-methylsulfonyl)amidide, butyl-3-methyl-1-imidazolium tetrafluoroborate, butyl-3-dimethyl-1,2-imidazolium tetrafluoroborate, ethyl-3-methyl-1-imidazolium tetrafluoro-borate, butyl-3-methyl-1-imidazolium hexafluorphosphate, butyl-3-methyl-1-imidazolium hexafluoroantimonate, butyl-3-methyl-1-imidazolium trifluoroacetate, ethyl-3-methyl-1-imidazolium triflate, butyl-3-methyl-1-imidazolium triflate, butyl-3-methyl-1-imidazolium methylsulfate, butyl-3-methyl-1-imidazolium butylsulfate, (hydroxy-2-ethyl)-1-methyl-3-imidazolium bis(trifluoromethylsulfonyl)amidide, (carboxy-2-ethyl)-1-methyl-3-imidazolium bis(trifluoromethylsulfonyl)amidide and N-butyl-N-methylmorpholinium bis(trifluoromethylsulfonyl)amidide. These salts can be used alone or in admixture.

The invention also relates to a plant for implementing the hydroformylation method as defined in the above description, said plant comprising (FIG. 1):

at least one reactor A1, optionally a mixer B3, at least one depressurization enclosure ("depressurizer") B1, and at least one decanter B2 for decantation of the polar phase containing at least the non-aqueous ionic solvent and at least the catalyst, which is recycled to reactor A1, in a separation section, at least one column A2 for separation of the crude reaction products and of the unreacted olefinically unsaturated compound to be hydroformylated, as well as the ligand present in the organic phase, as well as:

at least one line 1 for delivery of the feed to be hydroformylated and of the carbon monoxide/hydrogen mixture, at least one line 2 for transfer of the effluent from the reactor to depressurizer B1, at least one line 3 for sending to decanter B2 the mixture of organic effluent and of the ionic solvent contained in depressurizer B1, at least one line 4 for sending to the inlet of reactor A1 the gases from depressurizer B1, at least one line 5 allowing to send back to reactor A1 the polar phase containing at least the ionic liquid and the catalyst, separated in B2, at least one line 6 allowing to discharge from decanter B2 the crude reaction products, at least one line 7 for recycling to depressurizer B1 the unreacted olefinically unsaturated compound to be hydroformylated, as well as the ligand separated in column A2 (this recycle can optionally be carried out in mixer B3 located upstream from depressurizer B1 via a line 7'), at least one line 8 allowing to send the products collected at the bottom of column A2 to the remainder of the product fractionation train, at least one line 9 allowing the distillate to be discharged if need be, at least one line 10 for post-reaction addition of the ligand as described in the invention. The ligand can be added alone or in admixture in an organic solvent, optionally a line 10' for post-reaction addition of the ligand in mixer B3 located upstream from depressurizer B1.

The method and the plant according to the invention will be better understood from the description below, with reference to FIG. 1.

Figure 2:
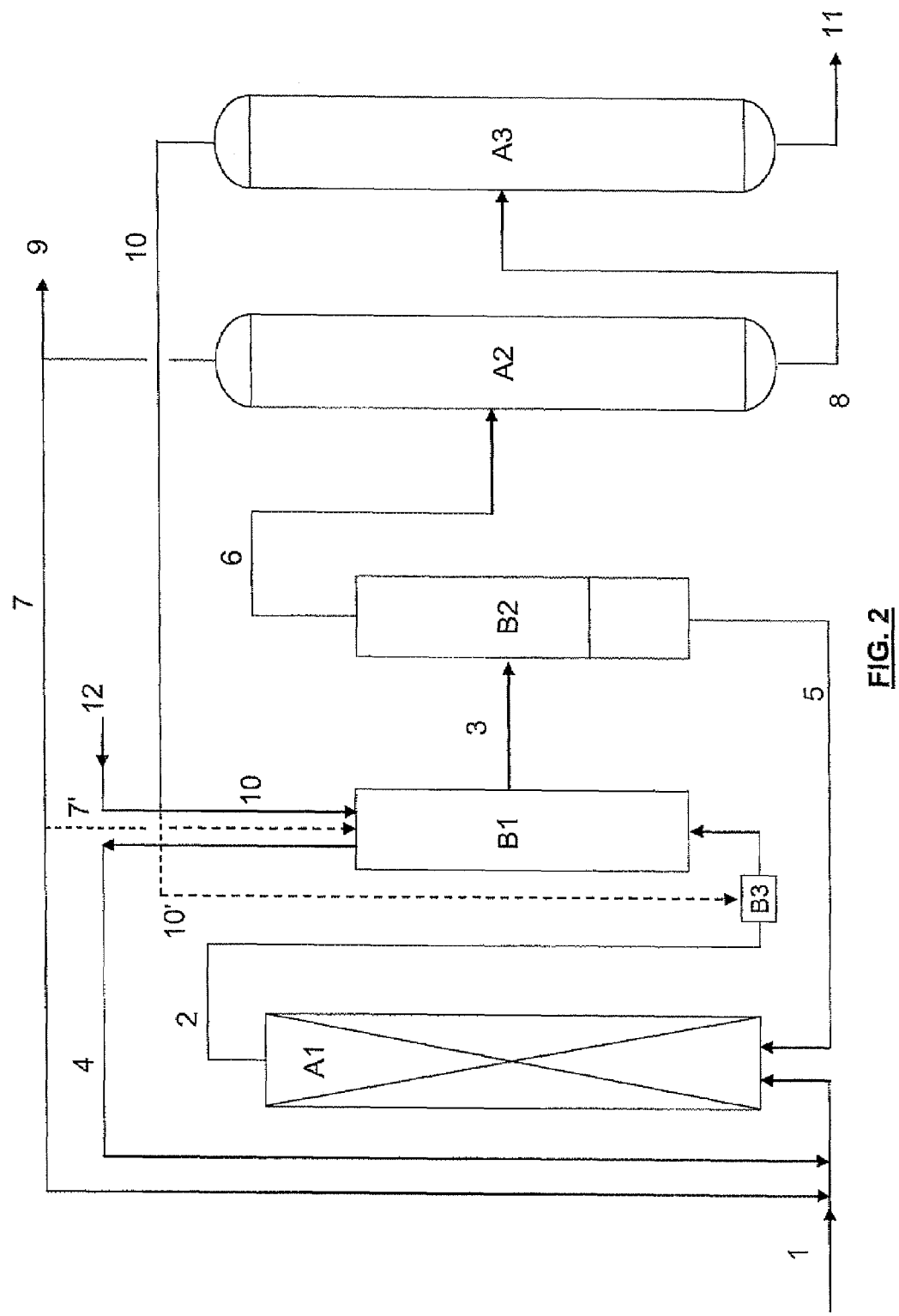

FIGS. 1 and 2 represent process schemes of the invention.

According to FIG. 1, the reaction is carried out in reactor A1 in the presence of the feed to be hydroformylated, which can be introduced through line 1, of the cobalt compound(s), of carbon monoxide and hydrogen, which can also be introduced through line 1, and in the presence of at least one non-aqueous ionic liquid. The ionic liquid can be introduced in the reactor at the start of the reaction. Optionally, fresh ionic liquid can be injected into reactor A1 during the reaction and used ionic liquid can be discharged from A1 (the ionic liquid injection and discharge means are not shown in FIG. 1).

The reaction heat is eliminated by means of techniques known to the man skilled in the art, not shown in FIG. 1.

At the reaction section outlet, the reactor effluent is sent, through line 2, into at least one depressurizer B1 wherein the pressure is lowered. Optionally, the reactor effluent can pass through a mixer B3 located upstream from depressurizer B1. Stirring can be maintained in B1, as well as in B3, either mechanical or using any other suitable means. The gases released through depressurization flow out through line 4 and they are sent back to the inlet of reactor A1 after being recompressed. During this depressurization stage, a ligand, as well as the unconverted olefins and possibly the solvent can be added to the reaction mixture directly in depressurizer B1 through line 7. They can alternatively be introduced into mixer B3 located upstream from depressurizer B1 through line 7'.

The effluent from depressurizer B1 is then sent to decanter B2 through line 3. In this decanter B2, the lower polar phase, which contains at least the ionic liquid and the catalyst, is separated from the mixture of products and from the organic solvent, and it is sent back to reactor A1 through line 5.

The upper organic phase separated in decanter B2 is sent to a distillation column A2 through line 6. In column A2, the unreacted olefinically unsaturated compound to be hydroformylated, the ligand and the optional solvent are separated at the head. As described above, they are recycled to depressurizer B1 through line 7 or, optionally, upstream therefrom in mixer B3 through line 7'. The crude reaction products collected at the bottom of A2 are sent to a specific fractionation train (not shown) through line 8.

Another plant for implementing the hydroformylation method as defined in the description is also possible as shown in FIG. 2. For example, this plant is particularly suited for a system with various components whose boiling points follow the increasing order as follows (Bp=boiling point):

$Bp_{olefin\ to\ be\ converted} < Bp_{ligand} \leq Bp_{solvent} < Bp_{reaction\ products}$ This plant comprises:

at least one reactor A1, optionally a mixer B3, at least one depressurization enclosure ("depressurizer") B1, and at least one decanter B2 for decantation of the polar phase containing at least the non-aqueous ionic solvent and at least the catalyst, which is recycled to reactor A1, in the separation section, at least one column A2 for separation of the unreacted olefinically unsaturated compound to be hydroformylated, at least one column A3 for separation of the crude reaction products (column bottom), of the ligand and of the optional solvent (column head), as well as:

at least one line 1 for delivery of the feed to be hydroformylated and of the carbon monoxide/hydrogen mixture, at least one line 2 for transfer of the effluent from the reactor to depressurizer B1, at least one line 3 for sending to decanter B2 the mixture of organic effluent and of the ionic solvent contained in depressurizer B1, at least one line 4 for sending to reactor A1 the gases from depressurizer B1, at least one line 5 allowing to send back to reactor A1 the polar phase containing at least the ionic liquid and the catalyst, separated in B2, at least one line 6 allowing to discharge from decanter B2 the crude reaction products, at least one line 7 for recycling to reactor A1 the unreacted olefinically unsaturated compound to be hydroformylated, at least one line 9 allowing the distillate to be discharged if need be, at least one line 10 for recycling to depressurizer B1 the ligand separated in column A3; this recycle can be optionally performed in a mixer B3 located upstream from depressurizer B1 (via 10'), at least one line 11 allowing to send the products from the bottom of column A3 to the remainder of the product fractionation train, and at least one line 12 for post-reaction addition of the ligand as described in the invention. The ligand can be added alone or in admixture in a solvent.

The method and the plant according to the invention will be better understood from the description below, with reference to FIG. 2.

According to FIG. 2, the reaction is carried out in reactor A1 in the presence of the feed to be hydroformylated, which can be introduced through line 1, of the transition metal compound(s), of carbon monoxide and hydrogen, which can also be introduced through line 1, and in the presence of at least one non-aqueous ionic liquid. The ionic liquid can be introduced in the reactor at the start of the reaction. Optionally, fresh ionic liquid can be injected into reactor A1 during the reaction and used ionic liquid can be discharged from A1 (the ionic liquid injection and discharge means are not shown in FIG. 2).

The reaction heat is eliminated by means of techniques known to the man skilled in the art, not shown in FIG. 2.

At the reaction section outlet, the reactor effluent is sent, through line 2, into at least one depressurizer B1 wherein the pressure is lowered. Optionally, the reactor effluent can pass through a mixer B3 located upstream from depressurizer B1. Stirring can be maintained in B1, as well as in B3, either mechanical or using any other suitable means. The gases released through depressurization flow out through line 4 and they are sent back to the inlet of reactor A1 after being recompressed. During this depressurization stage, a ligand coming from line 10, as well as the possibly solvent coming from column A3 (as it will be explains below) can be added to the reaction mixture directly in depressurizer B1 through line 10. Alternatively, this addition can be carried out in mixer B3 located upstream from the depressurizer, through line 10'.

The effluent from depressurizer B1 is then sent to decanter B2 through line 3. In this decanter B2, the polar phase, which contains at least the ionic liquid and the catalyst, is separated from the mixture of products and from the organic solvent, and it is sent back to reactor A1 through line 5.

The organic phase separated in decanter B2 is sent to a distillation column A2 through line 6. In column A2, the unreacted olefinically unsaturated compound to be hydroformylated is separated at the head. It is recycled to reactor A1 through line 7 or possibly discharged through line 9. A part thereof can also be recycled to the depressurizer through line 7'. The products collected at the bottom of A2 are then sent to a second distillation column A3 through line 8. In column A3, the ligand and the optional solvent are separated at the head. They are recycled to depressurizer B1 through line 10 or optionally upstream therefrom in mixer B3, through line 10'. The crude reaction products collected at the bottom of A3 are sent to a specific fractionation train (not shown) through line 11.

Example 2 hereafter illustrates the invention without limiting the scope thereof. Example 1 is given by way of comparison.

Example 1

Comparative

The hydroformylation reaction is carried out in a 100-ml Hastelloy® autoclave provided with a heater band allowing to control the temperature and with an efficient mechanical stirring system (gas-driven Rushton propellers with counterblades). 0.213 g dicobalt-octacarbonyl (i.e. 1.2 mmole cobalt), 2.0 molar equivalents of 2-methoxypyridine (0.273 g), 6 ml butyl-3-methyl-1-imidazolium bis(trifluoro-methylsulfonyl)amidide, 15 ml heptane and 15 ml C8 Dimate (feed from a Dimersol X®: 6% by weight of linear octenes, 58% by weight of methylheptenes and 34% by weight of dimethylhexenes) are fed into this autoclave, placed under atmospheric pressure of the hydrogen-carbon monoxide (1/1 by mole) synthesis gas, from which the air and humidity it contained have been removed. The pressure of the synthesis gas is brought to 10 MPa and the temperature to 130° C., and stirring is started (1000 rpm). The pressure in the reactor is kept constant throughout the reaction whose progress is controlled by measuring the synthesis gas consumption. After 6 hours reaction, the synthesis gas inflow is stopped and the reactor is left to cool down to 25° C. While maintaining stirring (250 rpm), the pressure is slowly lowered until it reaches the atmospheric pressure. Stirring is stopped and the reaction mixture is left to settle for one hour. After being discharged from the autoclave, the upper organic phase is slightly coloured and the lower phase is strong orange.

In order to evaluate the catalyst recycle efficiency, the ionic liquid phase recovered and isolated above is maintained in the reactor that is fed again with 15 ml heptane and 15 ml C8 Dimate. No cobalt octacarbonyl and no 2-methoxypyridine is added. The hydroformylation reaction is then conducted again for 6 hours in the same device and according to the same method of operation as described above.

The results of 8 consecutive cycles are summed up in the table hereunder:

| Cycle | Conversion (%) | Linear conversion (%) | Mono-branched conversion (%) | Two-branched conversion (%) | Aldehyde selectivity (%) |
|---|---|---|---|---|---|
| 0 | 89.0 | 100 | 94.0 | 77.7 | — |
| 1 | 79.6 | 99.7 | 86.5 | 63.4 | — |
| 2 | 71.1 | 98.9 | 79.0 | 52.0 | 78.5 |
| 3 | 67.1 | 98.1 | 74.5 | 48.5 | 80.4 |
| 4 | 57.7 | 95.2 | 65.1 | 38.5 | 82.1 |
| 5 | 52.6 | 92.0 | 59.8 | 33.6 | 90.2 |
| 6 | 46.4 | 85.2 | 52.4 | 29.8 | 88.6 |
| 7 | 37.4 | 78.0 | 43.1 | 21.1 | 92.9 |

Example 2

According to the Invention

The hydroformylation reaction is carried out in the same device and according to the same method of operation as described in Example 1, except that a predetermined amount of 2-methoxypyridine is added after each cycle to provide a L/Co ratio of 6:1. After this addition, the system is stirred for 15 min so as to allow all of the cobalt present in the organic phase to return into the ionic liquid phase. The reactor is then depressurized and the reaction mixture is left to settle for one hour. After removal from the autoclave, the upper organic phase is slightly colored and the lower phase is a strong orange. The ionic liquid phase thus obtained is fed again into the reactor, into which 15 ml heptane and 15 ml C8 Dimate are then introduced. The hydroformylation reaction is then conducted again in the same device and according to the same method of operation as described in the previous example with, of course, the addition of 2-methoxypyridine after each new cycle.

The results of 8 consecutive cycles are summed up in the table hereunder:

| Cycle | Conversion (%) | Linear conversion (%) | Mono-branched conversion (%) | Two-branched conversion (%) | Aldehyde selectivity (%) |
|---|---|---|---|---|---|
| 0 | 91.1 | 100.0 | 95.4 | 81.8 | — |
| 1 | 76.1 | 100.0 | 83.1 | 59.2 | 79.4 |
| 2 | 69.6 | 98.4 | 76.9 | 51.6 | 83.2 |
| 3 | 67.0 | 97.5 | 74.3 | 48.8 | 83.7 |
| 4 | 70.4 | 97.9 | 77.3 | 53.4 | 83.6 |

-continued

| Cycle | Conversion (%) | Linear conversion (%) | Mono-branched conversion (%) | Two-branched conversion (%) | Aldehyde selectivity (%) |
|---|---|---|---|---|---|
| 5 | 64.6 | 96.5 | 72.4 | 45.5 | 85.9 |
| 6 | 63.4 | 96.7 | 71.1 | 44.1 | 88.4 |
| 7 | 65.6 | 96.9 | 72.9 | 47.5 | 85.2 |

In conclusion, comparison of the results of Examples 1 and 2 shows an improved stability for the system using the method according to the invention.

The invention claimed is:

1. In a method for hydroformylating in the liquid phase olefinically unsaturated compounds, comprising conducting continuously:
   a hydroformylating reaction stage carried out in the presence of at least one non-aqueous ionic liquid comprising at least one salt of general formula $Q^+A^-$, wherein $Q^+$ represents a cation and $A^-$ represents an anion, and of a catalyst comprising at least one cobalt complex with at least one ligand L selected from among the Lewis bases,
   a depressurization stage,
   a decantation stage,
   and a recycling stage wherein the polar phase, which contains at least the ionic liquid and the catalyst, separated from the mixture of products and from the organic solvent in the decantation stage, is sent back to the reaction stage,
   the improvement comprising adding said ligand L, optionally in admixture with an organic solvent, in a post-reaction stage, to maintain a molar ratio L/Co in said post-reaction stage of above 2, wherein at least a partial addition of ligand L is continuously conducted downstream of the reaction stage and upstream of the decantation stage.

2. A method as claimed in claim 1 wherein, in said post-reaction stage, the molar ratio L/Co is below 100:1.

3. A method as claimed in claim 1 wherein, in said post-reaction stage, the molar ratio L/Co is below 25:1.

4. A method as claimed in claim 1, wherein at least one olefinically unsaturated compound to be hydroformylated, is selected from among the mono-olefins, and diolefins or from, olefinic compounds comprising one or more heteroatoms.

5. A method as claimed in claim 4, wherein a mixture of mono-olefins containing at most 30% terminal mono-olefins is treated.

6. A method as claimed in claim 5, wherein octene mixture having the following composition:
   linear octenes (2 to 10% by weight),
   methylheptenes (50 to 70% by weight),
   dimethylhexenes (25 to 35% by weight),
   other mono-olefins (1 to 3% by weight)
   wherein less than 10% are terminal mono-olefins, is treated.

7. A method as claimed in claim 1, wherein the concentration of the cobalt complex in the ionic liquid ranges between 0.1 mole per liter and 10 moles per liter.

8. A method as claimed in claim 1, wherein the hydroformylation reaction is carried out with a ratio of the partial pressures of hydrogen to carbon monoxide of 10:1 to 1:10, at a temperature ranging between 30° C. and 250° C., and at a pressure ranging between 1 MPa and 30 MPa.

9. A method as claimed in claim 1 wherein, in the depressurization stage, the reaction stage effluent is depressurized to a pressure below 1 MPa and at a temperature at most equal to 150° C.

10. A method as claimed in claim 1, wherein the gases released in the depressurization stage are recompressed and sent back to the reaction stage.

11. A method as claimed in claim 1, wherein the decantation stage comprises a lower polar phase which contains at least the ionic liquid and the catalyst, and said polar phase is separated in the decantation stage and is sent back to the reaction stage.

12. A method as claimed in claim 1, wherein the decantation stage comprises an upper organic phase the latter being separated in the decantation stage and sent to a distillation zone having a head zone and at least one of ligand, unconverted olefins and optional solvent is separated at said head zone.

13. A method as claimed in claim 12, wherein the ligand, the unconverted olefins and the optional solvent are added to the reaction mixture at the level of the depressurization stage.

14. A method as claimed in claim 1, wherein the reaction stage effluent passes through a mixing zone upstream from the depressurization stage.

15. A method as claimed in claim 14, wherein the ligand, the unconverted olefins and the optional solvent separated in the distillation stage are added to the reaction mixture at the level of said mixing zone.

16. A method as claimed in claim 12, wherein the upper organic phase separated in the decantation stage is sent to a first distillation zone where the unreacted olefinically unsaturated compound to be hydroformylated is separated at the head.

17. A method as claimed in claim 16, wherein the unreacted olefinically unsaturated compound to be hydroformylated, thus separated, is at least partly recycled to the reaction stage.

18. A method as claimed in claim 16, wherein the unreacted olefinically unsaturated compound to be hydroformylated, thus separated, is partly recycled to the depressurization stage.

19. A method as claimed in claim 16, wherein bottom products from the first distillation zone are sent to a second distillation zone where the ligand and the optional solvent are separated at the head.

20. A method as claimed in claim 19, wherein the ligand and the optional solvent separated at the head of the second distillation zone are recycled to the depressurization stage.

21. A method as claimed in claim 16, wherein the reaction stage effluent passes through a mixing zone upstream from the depressurization stage.

22. A method as claimed in claim 21, wherein the ligand and the optional solvent are separated at the head of a second distillation zone and are recycled at the level of said mixing zone.

23. A method as claimed in claim 1, wherein the catalyst precursor cobalt compounds are selected from among the cobalt salts and the carbonyl complexes.

24. A method as claimed in claim 23, wherein the catalyst precursor cobalt compounds are selected from among the acetylacetonates, alcoholates, carboxylates, dicobalt-octacarbonyl, cobalt-tetracarbonyl hydride and carbonyl clusters.

25. A method as claimed in claim 1, wherein the basic Lewis ligand is selected from among the oxygen-containing ligands, the sulfur-containing ligands, the nitrogen-containing ligands and the phosphorus-containing ligands, substituted or not by ionic functional groups.

26. A method as claimed in claim 25, wherein said ionic functional groups are selected from among the sulfonates, carboxylates, phosphates, ammoniums, phosphoniums and imidazoliums.

27. A method as claimed in claim 25, wherein the oxygen-containing ligand is selected from among the alcohols, phenols, ethers, ketones and acetals.

28. A method as claimed in claim 25, wherein the sulfur-containing ligand is selected from among the thiols, thiophenols, thioethers and disulfides.

29. A method as claimed in claim 25, wherein the nitrogen-containing ligand is selected from among the mono-amines, di-, tri- and poly-amines, imines, di-imines, pyridines, bipyridines, imidazoles, pyrroles and pyrazoles.

30. A method as claimed in claim 29, wherein the pyridine type ligand is selected from among the non-substituted pyridines and the pyridines substituted in position 2, 3, 4 or 5 by alkyl, aryl, aralkyl, alcoxy, aryloxy, hydroxy, halogenide, carboxyalkyl groups.

31. A method as claimed in claim 25, wherein the phosphorus-containing ligand is selected from among the phosphines, polyphosphines, phosphine oxides and phosphites.

32. A method as claimed in claim 1, wherein the organic solvent used in the post-reaction stage is selected from among the aliphatic hydrocarbons, cyclic or acyclic, saturated or unsaturated, and the aromatic or substituted aromatic hydrocarbons.

33. A method as claimed in claim 32, wherein the organic solvent is selected from among the n-paraffins, iso-paraffins and cyclic aliphatic hydrocarbons.

34. A method as claimed in claim 1, wherein the organic solvent consists of the olefinically unsaturated compound(s) to be converted.

35. A method as claimed in claim 1, wherein the salt of general formula Q+A− is at least a salt selected from among butyl-3-methyl-1-imidazolium bis(trifluoro-methylsulfonyl)amidide, ethyl-3-methyl-1-imidazolium bis(trifluoro-methylsulfonyl)amidide, triethylammonium bis(trifluoromethylsulfonyl)amidide, trimethylpropylammonium bis(trifluoromethylsulfonyl)amidide, butylimidazolium bis(trifluoromethylsulfonyl)amidide, butyl-3-dimethyl-1,2-imidazolium bis(trifluoro-methylsulfonyl)amidide, N-butyl-N-methylpyrrolidinium bis(trifluoromethylsulfonyl)amidide, N-ethyl-N-methylpyrrolidinium bis(trifluoro-methylsulfonyl)amidide, butyl-3-methyl-1-imidazolium tetrafluoroborate, butyl-3-dimethyl-1,2-imidazolium tetrafluoroborate, ethyl-3-methyl-1-imidazolium tetrafluoroborate, butyl-3-methyl-1-imidazolium hexafluorophosphate, butyl-3-methyl-1-imidazolium hexafluoroantimonate, butyl-3-methyl-1-imidazolium trifluoroacetate, ethyl-3-methyl-1-imidazolium triflate, butyl-3-methyl-1-imidazolium triflate, butyl-3-methyl-1-imidazolium methylsulfate, butyl-3-methyl-1-imidazolium butylsulfate, (hydroxy-2-ethyl)-1-methyl-3-imidazolium bis(trifluoromethylsulfonyl)amidide, (carboxy-2-ethyl)-1-methyl-3-imidazolium bis(tri-fluoromethylsulfonyl)amidide and N-butyl-N-methylmorpholinium bis(trifluoro-methylsulfonyl)amidide, used alone or in admixture.

36. A process according to claim 13, wherein said at least a partial addition of ligand L is continuously conducted in said mixing zone.

37. A process according to claim 1, wherein at least a partial addition of ligand L is continuously conducted in said depressurization zone.

38. A process according to claim 36, wherein at least a partial addition of ligand L is continuously conducted in said depressurization zone.

* * * * *